(12) United States Patent
Jacobs

(10) Patent No.: US 6,346,414 B1
(45) Date of Patent: *Feb. 12, 2002

(54) TRANSPOSITION ASSEMBLY FOR GENE TRANSFER IN EUKARYOTES

(75) Inventor: Eric Jacobs, Dorlisheim (FR)

(73) Assignee: Transgene S.A., Strasbourg (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/532,657

(22) PCT Filed: Apr. 14, 1994

(86) PCT No.: PCT/FR94/00419

§ 371 Date: Oct. 16, 1995

§ 102(e) Date: Oct. 16, 1995

(87) PCT Pub. No.: WO94/24300

PCT Pub. Date: Oct. 27, 1994

(30) Foreign Application Priority Data

Apr. 16, 1993 (FR) .............................. 93 04530

(51) Int. Cl.[7] .................. C12N 15/79; C12N 15/85; C12N 15/87

(52) U.S. Cl. ............... 435/320.1; 435/325; 435/455; 435/458; 435/462; 435/463; 514/44; 424/93.2; 536/23.1; 536/23.2

(58) Field of Search ............... 435/172.1, 172.3, 435/320.1, 235.1, 325, 363, 366, 455, 458, 462, 463, 471, 473, 476; 536/23.1, 23.2, 23.4, 23.72, 24.2; 424/205.1, 93.1, 93.2; 514/44; 935/9, 10, 22, 23, 32, 52, 56, 57, 66, 70, 71

(56) References Cited

U.S. PATENT DOCUMENTS 4,670,388 A   6/1987   Rubin et al. ............. 435/172.3
5,354,684 A * 10/1994   Hodgson et al. ......... 435/172.3

FOREIGN PATENT DOCUMENTS

| EP | 0 485 701 | 5/1992 |
| WO | WO88/03562 | 5/1988 |
| WO | WO88/03563 | 5/1988 |
| WO | WO92/07950 | 5/1992 |

OTHER PUBLICATIONS

Nucleic Acids Research, vol. 16, No. 22, 1988, Arlington, VA US, pp. 10561–10573 Xiong, Y. et al., "Ribosomal DNA Insertion Elements R1Bm and R2Bm Can Transpose in a Sequence Specific Manner to Locations Outside the 28S Genes."

Cell, vol. 57, No. 2, Apr. 21, 1989, Cambridge, NA US, pp. 335–345, Woodson, S.A. & Cech, T.R. "Reverse Self–Splicing of the Tetrahymena Group I intron: Implication for the Directionality of Splicing and for Intron Transposition."

Journal of Molecular Biology, vol. 212, No. 1, Mar. 5, 1990, pp. 37–52, Jakubczak, J.L. et al., "Type I (R1) and type II (R2) Ribosomal DNA Insertions of Drosophila Melanogaster Are Retrotransposable Elements Closley Related to those of Bombyx Mori."

(List continued on next page.)

Primary Examiner—Scott D. Priebe
(74) Attorney, Agent, or Firm—Burns, Doane, Swecker & Mathis, L.L.P.

(57) ABSTRACT

A transposition assembly for the transfer of a DNA fragment of interest into the ribosomal nuclear DNA of an eukaryotic cell. An insertion means, an eukaryotic cell and a pharmaceutical composition comprising said transposition assembly, as well as a method for the in vitro transfer of said DNA fragment, are also disclosed.

12 Claims, 1 Drawing Sheet

OTHER PUBLICATIONS

Sakaguchi (1990) Microbiol. Rev. 54(1): 66–74.*
McKinnon et al. (1985) Gene 40: 31–38.*
Verma et al., Nature, 389:239–242, 1997.*
Reeck et al. (1987) Cell 50: 667.*
Lewin (1987) Science 237: 1570.*
Webster's II New Riverside University Dictionary (1984) Soukhanov et al., eds., Houghton Mifflin Co., Boston, MA, p. 1279.*
Orkin et al. (Dec. 7, 1995) Report and Recommendation of the Panel to Assess the NIH Investment in Research on Gene Therapy.*

* cited by examiner

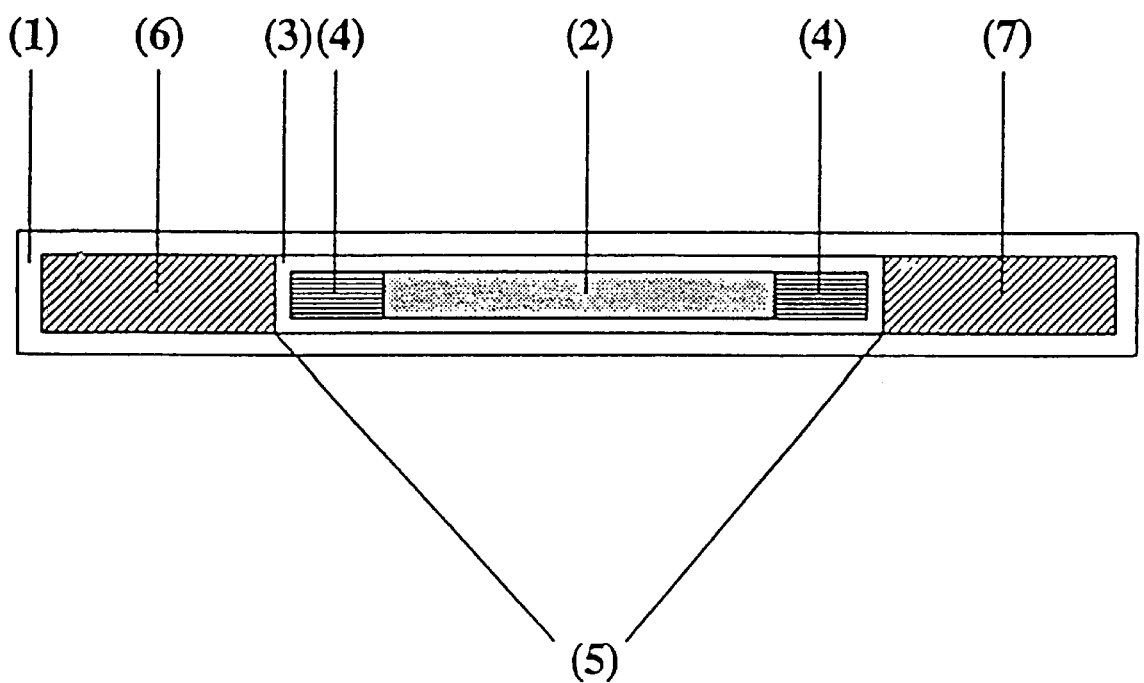

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: synthetic oligonucleotide (xi) SEQUENCE DESCRIPTION: SEQ ID NO:1:

CTATGACTCT CTTAAGGTAG CCAAA                                                  25

(2) INFORMATION FOR SEQ ID NO:2:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: synthetic oligonucleotide (xi) SEQUENCE DESCRIPTION: SEQ ID NO:2:

CTATGACTCT CT                                                                 12

(2) INFORMATION FOR SEQ ID NO:3:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: synthetic oligonucleotide (xi) SEQUENCE DESCRIPTION: SEQ ID NO:3:

TAAGGTAGCC AAA                                            13

(2) INFORMATION FOR SEQ ID NO:4:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic oligonucleotide (xi) SEQUENCE DESCRIPTION: SEQ ID NO:4:

GGGAAAAGCT TGCTAGCGGA TCTTGGTGGT AGTAGCAAAT ATTC              44

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide (xi) SEQUENCE DESCRIPTION: SEQ ID NO:5:

CCCCAAACTA GTTCTAGAGA GAGTCATAGT TACTCCCGCC GT                42

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic oligonucleotide (xi) SEQUENCE DESCRIPTION: SEQ ID NO:6:

CCCCAAACTA GTAAGGTAGC CAAATGCCTC GTCATCT                                37

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide (xi) SEQUENCE DESCRIPTION: SEQ ID NO:7:

AAAAGGGAAT TCGCTAGCAG ATCTCTGCTT CACAATGATA GGAAGAGC                    48

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: synthetic oligonucleotide (xi) SEQUENCE DESCRIPTION: SEQ ID NO:8:

TTTGGGGTAC CCACCCCCTT AAATATGGCG CTC                                    33

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: synthetic oligonucleotide (xi) SEQUENCE DESCRIPTION: SEQ ID NO:9:

TTTGGGGTAC CGCTGATTCC AAACTCGGGT G                                      31

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear

```
        (ii) MOLECULE TYPE: DNA (genomic)

(iii) HYPOTHETICAL: NO (iv) ANTI-SENSE: NO (vi) ORIGINAL SOURCE:
             (A) ORGANISM: synthetic oligonucleotide (xi) SEQUENCE DESCRIPTION: SEQ ID NO:10:

CCCCAAAGCT TAAACAAACC ACCGCATGGA                                                           30

(2) INFORMATION FOR SEQ ID NO:11:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (vi) ORIGINAL SOURCE:
             (A) ORGANISM: synthetic oligonucleotide (xi) SEQUENCE DESCRIPTION: SEQ ID NO:11:

CCCAAAAGCT TCAGTGCTCT GGATGTTAAA ATGG                                                      34
```

TRANSPOSITION ASSEMBLY FOR GENE TRANSFER IN EUKARYOTES

The present invention relates to a transposition assembly allowing the transfer of genes of interest into the genome of a cell or of a eukaryotic organism. Such an assembly is particularly useful for gene therapy purposes.

Numerous elements which can be employed by the integration of genes of interest into the eukaryotic genome have been described in the prior art publications. The conventional elements are either integrative vectors, for example retroviral vectors, or nonintegrative vectors, for example adenoviral vectors. However, these prior art vectors not only have advantages.

In fact, the retroviral vectors are integrated randomly into the cellular genome in a nonspecific manner. Thus the risk of insertional mutagenesis linked either to the inactivation of genes essential to the cell, or to the activation of oncogenes, which can give rise to a tumoral proliferation, is not to be neglected before contemplating their use in human gene therapy.

As far as the nonintegrative vectors are concerned, they have disadvantages linked to an instability on account of their nonintegration into the cellular genome, which necessitates their regularly repeated administration. Within the context of a gene therapy intended for man, in the long term this risks posing problems of immunization against the recombinant virus in regularly treated patients.

A third type of method, described more recently, allows the transfer of genes of interest by homologous recombination into a defined site of the cellular genome. However, the technique of homologous recombination again comes up against numerous technical difficulties. In addition, nonhomologous recombination events can equally be produced, so that the risk of insertional mutagenesis remains.

Moreover, the prior art has for a long time established the scheme of organization and of expression of ribosomal DNA (rDNA) in eukaryotes (Reeder, Trends Genet. 1990, 6, 390–395). Generally speaking, rDNA is formed by multiple copies of transcription units arranged in pairs. A transcriptional unit is composed of genes coding respectively for the 18S or 16S, 5-8S and 28S or 26S rRNAs, which enter into the constitution of the ribosome (below designated 18S rRNA gene etc.). Each gene is separated from the following by transcribed sequences whose exact role is still not defined. The three rRNA genes contained in a transcriptional unit are placed under the control of a unique promoter situated upstream in the nontranscribed region which separates one unit from the following. The units of rRNA are transcribed by the RNA polymerase I in a long molecule of precursor rRNA (pre-rRNA), which is then matured to produce the three principle types of rRNA associated to the ribosomal sub-units.

Numerous publications have reported the frequent presence of foreign genetic elements in the rDNA of eukaryotes. Among these genetic elements, introns of class I or II and retroposons, for example of class R1, R2 or R3, can be mentioned. The presence of these foreign elements can possibly inactivate a fraction of the transcriptional units of the rDNA. This does not seem to have serious consequences for the life of the organisms containing them. This phenomenon has particularly been described in the drosophila.

The introns of classes I and II are defined by the existence of preserved sequences forming structural elements characteristic of each of the classes such as defined by Cech and Bass (1986, Annu. Rev. Biochem 55, 599–629). Several authors have observed that certain introns of classes I and II are mobile. They can be copied and transferred specifically into copies of genes which are devoid of them (intron$^-$). This transposition process, at least in the majority of cases, turns out to be specific from the point of view of the insertion region.

Among the sixty or so introns of class I characterized until now, the majority are localized in the genes of the mitochondria and of the chloroplasts. The prior art mentions, in three cases only, the presence of mobile introns of class I in the nuclear genes. These introns have been demonstrated at the level of the rRNA genes of three species of lower eukaryotes, respectively the 26S rRNA genes of several strains of Tetrahymena (Kan et Gall, 1982, Nucl. Acids Res., 10, 2809–2821) and of the Carolina strain of *Physarum polycephalum*, (Muscarella et Vogt, 1989, Cell, 56, 443–454; this mobile intron being designated intron 3 below) and finally in the 16S rRNA gene of *Pneumocystis carinii* (Edman et al., 1988, Nature 334, 519–522). Until now, it has not been possible to demonstrate the presence of introns interrupting the rRNA genes of higher eukaryotes.

The intron 3 of *Physarum polycephalum* is the best characterized. Its mobility has been demonstrated experimentally (Muscarella et Vogt, 1989, Cell, 56, 443–454). This intron codes in part for a protein of 160 amino acids (Muscarella et al., 1990, Mol. Cel. Biol., 10, 3386–3396). The initiation codon of the putative translation is situated upstream of the intron, at the 3' end of the adjacent exon sequence at the 5' end of the intron. The protein encoded by the intron 3 is an endonuclease which recognizes a target sequence of at least 18 base pairs (bp) present in the insertion region and is capable of cleaving this sequence exactly at the level of the site of insertion of the intron 3 (Muscarella et Vogt, 1989, Cell, 56, 443–454).

The target sequence recognized by the endonuclease comprises the following sequence: 5' CTATGACTCTCT-TAAGGTAGCCAAA3' (SEQ ID NO:1). It is assumed that the transposition of the intron 3 is initiated by the recognition of the particular target sequence by the endonuclease specifically encoded by the intron 3, followed by a cutting of the two strands of the DNA molecule at the level of this particular sequence, thus liberating the insertion site. Then, by an exchange of fibers involving the flanking sequences at the 5' and 3' ends of the insertion site, copying of the intron sequence and recombination, the intron 3 is inserted into the copy of the intron$^-$ rRNA gene in a precise and site-specific manner. Once the intron 3 is inserted into a copy of the intron$^-$ gene, the target sequence recognized by the endonuclease is interrupted by the intron sequence in the following manner: 5' CTATGACTCTCT (SEQ ID NO:2) intron 3 TAAGGTAGCCAAA3' (SEQ ID NO:3).

On the other hand, retroposons equally seem to be present in the rDNA of certain eukaryotes. Generally speaking the retroposons form a very huge and very heterogeneous group, especially at the level of their nucleotide sequence. Retroposon is understood as meaning elements related to the retroviruses, but devoid of long terminal repeats (LTR). They comprise one or more open reading frames capable of coding for proteins having a homology with retroviral proteins, such as, for example, reverse transcriptase (Jakubczak et al., 1991, Proc. Natl. Acad. Sci. USA, 88, 3295–3299).

In a certain number of nonmammalian eukaryotes, especially insects, retroposons having a remarkable specificity of insertion have been found, localized at the level of the rRNA genes. The mobility of certain of these has been observed. Several families (especially R1, R2 and R3) have been defined as a function of their specific insertion region into the rRNA genes.

The retroposons of the classes R1 and R2 are especially illustrated by the retroposons R1Bm and R2Bm of *Bombyx mori* (Xiong and Eickbush, 1988, Cell, 55, 235–246; Xiong and Eickbush, 1988, Mol. Cell. Biol., 8, 114–123; Xiong et al., 1988, Nucl. Ac. Res., 16, 10561–10573) and the retroposons R1Dm and R2Dm of *Drosophila melanogaster* (Jakubczak et al., 1990, J. Mol. Biol., 212, 37–52). They contain air open reading frame capable of coding for a protein of great size whose central part has a homology with the reverse transcriptase family. Xiong and Eickbush (1988, Cell, 55, 235–246) report that the protein encoded by the retroposon R2Bm of Bombyx mori moreover has an endonuclease activity. This nuclease recognizes and cleaves a target sequence contained in the insertion region of R2Bm situated in the 28S rRNA gene of the insect genome.

A novel class of ribosomal retroposons, designated R3, has recently been demonstrated. Protein encoded by this element has still not been characterized. However, the specific insertion region of the element R3 into the rDNA of *Scaria coprophila* has been described (Kerrebrock et al., J. Mol. Biol., 1989, 210, 1–13).

Beside retroposons, there are a large number of mobile genetic elements which have sometimes been designated under the name of retroposons by the authors describing them, but of which it has still not been shown that they code for a protein having a homology with the family of retroviral proteins, especially reverse transcriptase. This type of elements has equally been found at the level of well-defined sequences of rRNA genes of organisms containing them (see, for example, Back et al., 1984, EMBO J., 3, 2523–2529).

Surprisingly, it has now been found that on the one hand the target sequences recognized by the endonucleases encoded by the two mobile genetic elements for which the data are available (intron 3 of *Physarum polycephalum* and retroposon R2Bm of *Bombyx mori*) and on the other hand the insertion regions of certain mobile genetic elements of which it has still not been shown that they code for an endonuclease and which have been disclosed in the prior art (Jakubczak et al., 1991, Proc. Natl. Acad. Sci. USA, 88, 3295–3299; Paskwitz et Collins, 1989, Nucleic Acid Res. 17, 8125–8133; Kerrebrock et al., 1989, J. Mol. Biol., 210, 1–13; Kan and Gall, 1982, Nucleic Acid Res., 10, 2809–2821; Edman et al., 1988, Nature, 263, 519–522), are conserved in the rRNA genes of various mammals, especially man and the mouse. Thus, the sequences of insertion regions of mobile introns of Tetrahymena, of Pneumocystis carinii and of Physarum polycephalum, and of R2Bm retroposons of *Bombyx mori,* and R3 of *Scaria coprophila* are conserved identically in the rRNA genes of mammals. On the other hand, the sequences of the insertion region of the retroposons R1Dm and R1Bm are homologous but nonidentical to a sequence present in the mammalian 28S rRNA gene.

Consequently, the present invention relates to a transposition assembly intended for the transfer of a DNA fragment of interest into the genome of a eukaryotic host cell, which comprises an integration cassette, essentially formed by a mobile genetic element in the midst of which is inserted the said DNA fragment of interest; the said integration cassette being capable of being integrated in a site-specific fashion into a specific insertion site situated in the ribosomal nuclear DNA of the said host cell.

A transposition assembly according to the invention has the advantage of allowing the integration of a DNA fragment of interest into a defined and nonessential region of the cellular genome. Such an assembly is especially useful for gene therapy purposes.

For the purposes of the present invention, the integration cassette must comprise a mobile genetic element which has the capacity for integrating itself by a site-specific mechanism into the nuclear rDNA, in particular at the level of the 28S, 18S or 5-8S rRNA gene. More precisely, this mobile genetic element must integrate itself into an insertion site situated in an insertion region of which the sequence is conserved in an identical or nonidentical manner in the nuclear rDNA of the host cell.

For a better understanding, it is specified that the term "insertion site" defines the place between 2 nucleotides where a mobile genetic element is inserted. In the same way, "insertion region" is understood as meaning the nucleotide sequences at the 5' and 3' end of the insertion site which are required for the site-specific transposition. Generally speaking, each mobile genetic element possesses an insertion region which is specific to it. As mentioned above for the retroposons R1Bm and R1dm, it is not required that the insertion region in the host cell comprises in an identical manner the sequences of the natural insertion region (in the organism of origin). Thus, the sequence of the insertion region of the said mobile genetic element in the eukaryotic host cell will present a degree of homology with the sequence of the natural insertion region greater than 80%, advantageously greater than 90% and preferably greater than 95%.

The mobile genetic element is advantageously selected from amongst mobile introns of class I or II, and retroposons such as the retroposons of class R1R2 [sic] or R3.

A genetic mobile element can be formed by a functional fragment or a variant of the said element. Functional fragment is understood as meaning any fragment which has conserved the capacity of being integrated of the complete element. A variant can comprise one or more mutations with respect to the natural nucleotide sequence of the element, especially the substitution, addition or deletion of one or more nucleotides, on condition that these mutations do not alter the function.

More particularly, the mobile genetic element is selected from amongst:

the intron 3 of *Physarum polycephalum,* Carolina strain, a fragment or a variant of the said intron, the mobile intron of class I of Tetrahymena, a fragment or a variant of the said intron, the mobile intron of class I of *Pneumocystis carinii,* a fragment or a variant of the said intron, the retroposon of R2Bm of *Bombyx mori,* a fragment or a variant of the said retroposon and, the retroposon R3 of *Scaria coprophila,* a fragment or a variant of the said retroposon.

The presence in this mobile genetic element of all or part of an open reading frame capable of coding for an integrase is a preferred characteristic.

Generally speaking, integrase is understood as meaning a protein having an enzymatic activity allowing it to participate directly or indirectly in the trans-position of the mobile genetic element specifically at the level of its insertion site in the nuclear rDNA of a eukaryotic cell.

Advantageously, the integrase can be especially formed by:

(1) a protein having an endonuclease activity capable of recognizing a specific target sequence included in the insertion region of the mobile genetic element which codes for it and of cleaving the said target sequence, or (2) a protein having a homology with the family of reverse transcriptases.

It is possible to mention, for example, the endonuclease encoded in part by the intron 3 of *Physarum popycephalum*. This endonuclease initiates the transposition of the intron 3 on recognizing its target sequence and cleaving the DNA molecule at the level of this specific sequence.

It is equally possible to mention the protein encoded by the retroposon R2Bm of *Bombyx mori*. The endonuclease activity of the said protein is probably involved in the transposition of R2Bm at the level of its specific insertion region, but by a mechanism which is not known to date.

The DNA fragment of interest can be introduced into the mobile genetic element by the conventional techniques of genetic engineering. It can be integrated in or outside of the open reading frame coding for a possible integrase.

According to a particularly advantageous aspect of the invention, the DNA fragment of interest is inserted in the open reading frame in order to prevent the expression of the integrase. This introduces a security feature to avoid the uncontrolled propagation of the integration cassette in the genome of the host cell.

In this case, the specific integrase of the mobile genetic element employed in the transposition assembly according to the invention should be supplied to the host cell in a transitory manner during a time which is sufficiently long to allow the transposition of the integration cassette into its specific insertion region. The means of supplying a protein in trans to a eukaryotic cell are numerous and known to the person skilled in the art.

For example, the transposition assembly according to the invention can be introduced into a vector (such as defined below), moreover comprising an expression cassette of the specific integrase of the mobile genetic element present in the transposition assembly.

In an alternative manner, the eukaryotic host cell can be transfected in parallel with a helper vector comprising an expression cassette of the integrase or the integrase can be supplied in purified form to the host cell.

The DNA fragment of interest can be any fragment capable of being transcribed to RNA to produce an antisense RNA for example a complementary RNA sequence of a pathogenic gene capable of forming a duplex with a pathogenic transcript in order to inhibit the translation to pathogenic protein. A pathogenic gene is:

(1) a gene which is not present in the eukaryotic cells, for example a gene present in the genome of a pathogenic organism (bacteria, virus or parasite), or (2) a homologous gene or a mutated homologous gene, for example an oncogene, which is present but normally not expressed in the normal eukaryotic cells and whose abnormally induced expression can cause a disorder such as cancer.

In an alternative fashion, the DNA fragment of interest can code for a protein of interest and, in a preferred manner, a protein whose absence of expression or expression in abnormal quantity or in mutant form is associated with a genetic disorder.

The DNA fragment of interest can code for a mature protein or a precursor of this. In the first case, it comprises the sequence coding for a mature protein allowing the expression of the protein in intracellular fashion. In the last case, the DNA fragment of interest can equally include a signal sequence allowing the secretion of the said protein of the host cell. The DNA fragment of interest can code for a chimeric protein arising from the fusion of various sequences of origin.

The examples of proteins which can be encoded by the DNA fragment of interest comprise:

cytokines, such as alpha interferon, gamma interferon and different types of growth factors, membrane receptors, such as the receptors involved in the transmission of signals from the surface to the interior of cells and the receptors recognized by pathogenic organisms, such as the CD4 receptor present at the surface of T lymphocytes and recognized by the envelope glyco-protein of the HIV virus (Human Immunodeficiency Virus), enzymes, such as the ribonucleases and the thymidine kinase (TK) of the type I herpes simplex virus (HSV-1). The latter has a superior affinity with respect to the mammalian cell TK enzyme for certain analogs of nucleosides, such as acyclovir or gancyclovir. The enzyme TK-HSV-1 converts the analogs into precursors of nucleotides. These toxic precursors are then incorporated into the DNA of cells in a state of replication. This incorporation allows the cells in division, such as cancer cells, to be killed specifically, inhibitors of enzymatic activity, such as alpha 1 antitrypsin, antithrombin III, protein C and specific protease inhibitors of a pathogenic organism, coagulation factors, such as factor VIII, factor IX and thrombin, proteins involved in ionic channels, such as the protein CFTR (Cystic Fibrosis Transmembrane Conductance Regulator), proteins capable of inhibiting the activity of a protein produced by a pathogenic gene, such as the suppressor antigen of tumor p53, variants of pathogenic proteins mutated so as to alter their biological function, such as trans-dominant mutants of the regulator protein TAT of the HIV virus capable of competing with the native viral protein for linkage to the target sequence, preventing activation of the expression of the viral genes and, antigenic epitopes allowing immunity of the host cell to be increased.

The DNA fragment of interest can be mutated so as to allow the expression of a protein of interest whose biological properties are modified, for example a variant of alpha 1 antitrypsin whose methionine residue in position 358 of the active site has been replaced by a leucine. Such a variant is functional under oxidation conditions such as inflammation conditions.

Once the integration cassette is introduced into the rDNA of the host cell, the DNA fragment of interest can be placed under the dependence of the promoter of the transcriptional unit of the rDNA of the host cell. Alternatively, the DNA fragment of interest can be placed under the control of appropriate expression elements inserted into the mobile genetic element. Expression here signifies transcription to RNA and/or translation of this RNA to protein.

According to this alternative, the control elements of the expression especially comprise an appropriate promoter. Such promoters are well known to the person skilled in the art and are inserted upstream of the DNA fragment of interest by the conventional techniques of genetic engineering.

The promoter retained can be a promoter recognized by RNA polymerase I, so as to favor the expression of the DNA fragment of interest, after integration of the integration cassette into the rRNA genes of the eukaryotic host cell. For example, the DNA fragment of interest can be placed under the control of regulation elements included in the nontranscribed regions of the rDNA involved in the transcription of the rRNA genes. Such promoters will be chosen so as to be functional in the eukaryotic host cell which has been retained.

In an alternative manner, the promoter retained can be a promoter recognized by RNA polymerase II. Such promoters are well known to a person skilled in the art. The promoter can be isolated from a cellular gene or from a virus. It can be ubiquitous, allowing a permanent expression of the DNA fragment of interest in all the types of host cells. The term promoter equally includes a regulatable promoter, for example a tissue-specific promoter. It is possible especially to mention the promoter of the HMG gene (hydroxymethylglutaryl coenzyme A reductase), of the TK gene of the HSV-1 virus, of the SV40 virus (Simian virus 40), the promoters EIII and MLP (Major Late Promoter) of the adenovirus, the LTR of the MoMuLV virus (Moloney Murine Leukemia Virus), the promoter of the FIX gene which confers a liver-specific expression or the promoter of specific immunoglobulin genes of lymphocyte cells.

In an advantageous manner, the transposition assembly moreover comprises an integration cassette of elements allowing or favoring the site-specific integration of this cassette. According to a particular mode of the invention, especially when the mobile genetic element employed is a mobile intron of class I or II, the transposition assembly according to the invention moreover comprises:

at the 5' end of the integration cassette a region of at most 10 kb, having at least 80% homology with the sequences of the rRNA gene of the host cell immediately adjacent at the 5' end at the said insertion site; and at the 3' end of the integration cassette a region of at most 10 kb having at least 80% homology with the sequences of the rRNA gene of the host cell immediately adjacent at the 3' end at the said insertion site. In fact, it can be advantageous to place the said integration cassette in an rDNA environment, particularly when the transposition involves a phenomenon of exchange of strands as has been shown especially for the intron 3. The exchange of strands involves the intron+donor sequences (of the transposition assembly) and the intron-recipient sequences (of the host cell). Only the integration cassette will be transposed into the genome of the host cell. The sequences of the rRNA gene immediately adjacent at the 5' and 3' ends of the insertion site intervene uniquely in the transposition process.

In order to favor the transposition of the integration cassette, it will be preferred to have perfect homology between the donor and recipient sequences involved in the strand exchange. Thus, a preferred transposition assembly will moreover comprise:

at the 5' end of the integration cassette a region of at most 10 kb, having 100% homology with the sequences of the rRNA gene of the host cell immediately adjacent at the 5' end at the said insertion site; and at the 3' end of the integration cassette a region of at most 10 kb, having at least 100% homology with the sequences of the rRNA gene of the host cell immediately adjacent at the 3' end at the said insertion site.

The sequences of the rRNA gene immediately adjacent at the 5' and 3' ends of the insertion site can be isolated according to the classical techniques of genetic engineering, for example by cloning or PCR (Polymerase Chain Reaction) or chemical synthesis. More particularly, these sequences will have a length of at most 10 kb, advantageously at most 3 kb and preferably at most 0.4 kb.

The present invention equally relates to a means of introduction of a transposition assembly according to the invention into a eukaryotic cell. Such means consisting in introducing a nucleic acid into a eukaryotic cell are generally known to a person skilled in the are.

For the purposes of the present invention, the transposition assembly according to the invention can be introduced in a means of introduction selected from amongst the delivery vehicles of the liposome and synthetic cationic lipid type and the cloning and expression vectors classically utilized in the eukaryotic cells. Encapsulation in a delivery vehicle and the techniques of cloning in vectors are classical techniques known to the person skilled in the art. However, other protocols allowing a nucleic acid to be introduced into a cell can equally be employed, such as, for example, calcium phosphate precipitation, the DEAE-dextran technique, direct injection of the nucleic acid into a cell or the bombardment of gold microparticles covered with nucleic acid in the cells of an animal. The nucleic acid can be introduced in supercoiled, circular or linear form.

Advantageously, the means of introduction according to the invention is a vector comprising the elements appropriate for its maintenance in the host cell for a time which is sufficiently long to allow the transfer of the integration cassette into the insertion region. Such a vector has to be capable of entering a higher eukaryotic cell, of remaining, preferably, in extra-chromosomal form and of being maintained in the cell for a time which is sufficiently long to allow the transposition of the integration cassette into the genome of the host cell. Such a vector can be in the form of a plasmid or of a viral vector.

Preferably, the means of introduction according to the invention is a vector of the nonintegrative type. It is possible to mention a vector derived from the herpes simplex virus or from an adenovirus. Particularly preferably, the means of introduction according to the invention is a vector derived from an adenovirus, such as, for example, type 5 adenovirus.

According to an advantageous mode and as recalled above, the means of introduction according to the invention can moreover contain an expression cassette allowing the production of the specific integrase of the transposition assembly.

Such an expression cassette comprises the DNA fragment coding for the said integrase, placed under the control of appropriate elements allowing its expression. Appropriate elements allowing its expression is understood as meaning the whole of the elements allowing the transcription of the said fragment of DNA to mRNA and the translation of the mRNA to protein. These elements especially comprise an appropriate promoter, preferably a promoter recognized by the RNA polymerase II and allowing a strong and ubiquitous expression, for example the promoter SV40.

The means of introduction according to the invention can moreover comprise an expression cassette allowing the expression of a selection gene allowing the detection and isolation of the host cells comprising the said means of introduction. In the context of the invention, the gene coding for the selection marker can be under the control of appropriate elements allowing its expression in the host cell, such as defined above.

The invention is equally related to an in vitro transfer process of a DNA fragment of interest into the genome of a eukaryotic host cell at the level of the ribosomal nuclear DNA, according to which a transposition assembly according to the invention or a means of introduction according to the invention is introduced into the said host cell.

Advantageously, it is moreover possible to supply the specific integrase of the transposition assembly according to the invention to the host cell in the in vitro process according to the invention.

The invention equally relates to a eukaryotic cell comprising a transposition assembly according to the invention or a means of introduction according to the invention. The said cell will advantageously be a mammalian cell, and preferably a human cell.

The present invention equally relates to a pharmaceutical composition comprising by way of therapeutic agent, a transposition assembly according to the invention, a means of introduction according to the invention or a cell according to the invention, in association with a carrier which is acceptable from a pharmaceutical point of view.

The pharmaceutical composition according to the invention is particularly intended for the preventive or curative treatment of disorders such as:

- genetic disorders, such as, for example, hemophilia or mucoviscidosis,
- cancers, such as, for example, those induced by oncogenes or viruses,
- retroviral disorders, such as, for example, AIDS (Acquired Immunodeficiency Syndrome), and
- recurrent viral disorders, such as, for example, viral infections caused by the herpes virus.

A pharmaceutical composition according to the invention can be manufactured in a conventional manner. In particular, a therapeutically efficacious quantity of a therapeutic agent is united with a support such as a diluent. A composition according to the invention can be administered by any conventional route in use in the field of the art, in particular by the subcutaneous route, by the intramuscular route, by the intravenous route or by the intratracheal route. Administration can take place in a single dose or repeated one or more times after a certain time interval. The route of administration and the appropriate dose vary as a function of various parameters, for example of the individual treated or of the DNA fragment of interest. A pharmaceutical composition can moreover comprise an adjuvant acceptable from a pharmaceutical point of view.

Advantageously, the pharmaceutical composition according to the invention moreover comprises an integrase or an integrase expression cassette.

The invention equally extends to a method of treatment according to which a therapeutically efficacious quantity of a transposition assembly according to the invention, a means of introduction according to the invention or a cell according to the invention is administered to a patient having need of such a treatment.

BRIEF DESCRIPTION OF THE DRAWINGS

The invention is illustrated below by reference to FIG. 1 which schematically represents a transposition assembly (1) (large blank box) which comprises from 5' to 3': the sequences of the rRNA gene (6) (hatched box) at the 5' end of the insertion site (5) (black lines), an integration cassette (3) (small blank box) formed by a mobile genetic element (4) (horizontally ruled box) in the midst of which is inserted a fragment of DNA of interest (2) (stippled box) and the sequences of the rRNA gene (7) (hatched box) at the 3' end of the insertion site (5).

EXAMPLES

Example 1

Construction of a Transposition Assembly for Site-specific Integration into the 28S rRNA Genes of a Human Cell, Employing Intron 3 of *Physarum polycephalum* Carolina Strain The example refers to a transposition assembly which comprises (1) the intron 3 modified so as to create a unique site of restriction XhoI in the intron sequence. The site XhoI will allow a fragment of DNA of any interest whatsoever to be introduced. In fact, the DNA fragment of interest can be isolated so as to have sticky ends compatible with the ends generated by an XhoI digestion (restriction fragment XhoI or SaiII or XhoI-SalI or addition of XhoI and/or SalII linkers or mutagenesis directed in order to create the required sites XhoI and/or SalI). Alternatively, the cloning site XhoI can be treated, for example, with Mung bean nuclease in order to generate free ends between which it is possible to clone any fragment of DNA of interest with free ends. The DNA fragment of 0.94 kb comprising the intron 3 can be isolated, especially by cloning or PCR, or synthesized chemically, and (2) The sequences immediately adjacent at the 5' and 3' ends at the insertion site of the intron 3. These sequences are isolated from the human 28S rRNA gene comprising the insertion region of the intron 3 perfectly conserved. The mobile intron will thus be placed in an rDNA environment. The exchange of strands will involve perfectly homologous sequences since any two are of human origin (donor sequences of the integration cassette and recipient sequences of the human host cell). The sequences immediately adjacent at the 5' and 3' ends can be isolated, especially by cloning or PCR, or synthesized chemically.

1. Cloning by PCR of the Sequences Immediately Adjacent at the 5' and 3' Ends at the Site of Insertion of the Intron 3 Starting from the 28S Human rRNA Gene Primers have been defined with the aid of the sequence of the human 28S rRNA gene included in the DNAstar donor bank (reference: HUMRGM, the reported sequence extending from the position+1 to the position+5025). The insertion site and the insertion region of the intron 3 have been located (such as reported in Muscarella and Vogt, 1989, Cell, 56, 443–454). The insertion site is included between the nucleotides 3742 and 3743 of the human 28S rRNA gene.

A first fragment of DNA corresponding to the fragment extending from the position 2324 to the position 3742 of the human 28S rRNA gene is generated by PCR. The primer corresponding to the coding strand (position 2324 to 2349) is reported in SEQ ID NO:4. It moreover comprises a free 5' end bearing the sites HindIII and NheI. The reverse primer is described in SEQ ID NO:5 and comprises a 5' end including the sites SpeI and XbaI. Amplification is carried out with the polymerase of Thermus Aquaticus (Perkin Elmer Cetus) according to the standard conditions indicated by the manufacturer. The matrix used is human DNA prepared conventionally. The amplified product is examined on agarose gel and sequenced.

The second fragment of human 28S rRNA gene is likewise isolated by PCR. It is the portion of gene extending from position 3743 to 4438. The two oligo-nucleotides employed are reported in SEQ ID NOS:6 and 7. The first primer comprises at its 5' end a SpeI site while the reverse primer contains from 5' to 3' the EcoRI, NheI and BglII sites. The amplification reaction is carried out starting from genomic human DNA prepared conventionally, under the standard conditions currently employed by the specialist. The PCR fragment thus generated is examined on agarose gel and sequenced.

The fragment comprising 1 kb of human sequences immediately adjacent at the 5' end at the insertion site of the intron 3 is digested by the enzymes HindIII and SpeI. The fragment comprising the sequences immediately adjacent in 3' is digested by SpeI and EcoRI. The two fragments are then ligated in the plasmid pUC 19 (Yanisch-Perron et al., 1985, Gene, 33, 103–119) previously digested by HindIII and EcoRI. The ligation mixture is transformed in the strain *Escherichia coli* 5K (*E. coli* 5K) giving rise to the plasmid pHREI.

2. Cloning of the Intron 3 of Modified *Physarum polycephalum*

The intron 3 (0.94 kb) is isolated by the PCR technique. The primers are fixed starting from sequence data reported in the literature (Muscarella et al, 1990, Mol. Cell. Biol., 10, 3386–3996; Johansen et al, 1992, Curr. Genet., 22, 297–304). The primers are described in SEQ ID NOS:8 and 9. They both comprise a KpnI site in their 5' region.

The amplification reaction is carried out starting from a genomic DNA bank of *Physarum polycephalum*, Carolina strain (Muscarella et Vogt, 1989, Cell, 56, 443–454), applying the standard conditions known to the specialist. After amplification, the size of the fragment obtained is checked on agarose gel and its sequence is examined.

The PCR fragment is digested by KpnI and cloned in the KpnI site of the vector pUC19 to give pINEI.

The vector pINEI is digested by NheI, a unique site situated in the intron 3 of *Physarum polycephalum*. The linearized pINEI vector is treated with Mung bean nuclease and ligated to an XhoI linker (Stratagene). The vector resulting from this is designated pINEII and thus comprises a unique XhoI site for the insertion of a fragment of DNA of interest.

3. Insertion of the Intron 3 of *Physarum polycephalum* (XhoI) into a Human 28S rRNA Gene Environment The fragment KpnI obtained by digestion of pINEII is treated with the T4 polymerase to give a fragment with three ends whose 5' and 3' ends correspond exactly to those of the intron.

In parallel, pHREI is digested by the enzymes XbaI and SpeI, then treated with the Mung bean nuclease (according to the technique reported in Sambrook et al, 1989, Cold Spring Harbor Press). This generates a large fragment comprising the majority of the vector pHREI, of which the free ends correspond respectively to the nucleotides in position 3742 and 3743 of the human 28S rRNA gene.

The fragment formed from pINEII comprising the intron 3 of *Physarum polycephalum* is ligated to the vector pHREI treated as indicated above to give the vector pHREII. After introduction of a fragment of DNA of interest, the vector pHREI will thus comprise a transposition assembly allowing the insertion of an integration cassette (the intron 3 comprising a fragment of DNA of interest) into the human 28S rRNA gene.

Example 2

Construction of an Adenoviral Vector for the Integration of the Neomycin Gene into the Human Genome An adenoviral vector is constructed comprising:
(1) the intron 3 of *Physarum polycephalum* (Xho$^+$) at the level of which is introduced a first expression cassette allowing the expression of the neo gene,
(2) a second expression cassette, that of the site-specific endonuclease IPpo, encoded in part by the intron 3. The second expression cassette will allow the production of the endonuclease IPpo for a time which is sufficiently long to allow the transposition of the integration cassette into the genome of the host cell. The initiator codon of the translation of IPpo is situated in the exon sequence at the 5' end of the intron 3 in the 26S rRNA gene of *Physarum polycephalum*. The sequence immediately adjacent at the 5' end to the isolated insertion site of the human 28S rRNA gene does not contain the ATG initiator present in the equivalent region of Physarum and
(3) the appropriate elements for the maintenance of the vector in the host cell for a time which is sufficiently long to allow the transposition of the integration cassette.

1. Construction of the Expression Cassette of IPpo

A fragment of 167 nucleotides containing the poly A region of SV40 (Fitzgerald and Shenk, 1981, Cell, 24, 251–260) is synthesized in the form of a HindIII-EcoRI fragment with the aid of an automatic synthesizer (Milligen 7500). A BglII site is introduced just upstream of the EcoRI site.

A HindIII-BamHI fragment of pMSG-CAT (Pharmacia) comprising the early promoter of the SV40 virus is isolated. The HindIII-EcoRI synthetic fragment and the HindIII-BamHI fragment are introduced into a derivative of the vector pUC19 (HindIII$^0$) digested by BamHI and EcoRI. The derivative is obtained after digestion of A fragment of DNA comprising the sequence coding fro the nuclease IPpo is isolated in the form of a PCR fragment. The sequence reported in the prior art (Muscarella et al., 1990, Mol. Cell. Biol., 10, 3386–3396) has allowed two primers to be defined which are respectively described in SEQ ID NOS: 10 and 11. The 2 oligo-nucleotides comprise a HindIII site at their 5' end. Amplification is carried out under the standard conditions known to the specialist starting from a genomic DNA bank of *Physarum polycephalum*, Carolina strain.

The PCR fragment generated, after examination on agarose gel and sequencing, is digested by HindIII and introduced into the unique HindIII site of the vector pSV40EI. A clone having a correct orientation of the sequence coding for IPpo with respect to the promoter SV40 is identified. The clone is designated pSV40EII.

2. Cloning of the Expression Cassette of the Endonuclease IPpo in the Vector pHREII The vector pHREII is digested by BglII and treated with T4 polymerase. The vector pSV40EII is digested by the enzymes PstI and BglII. The fragment PstI-BglII comprising the expression cassette of IPpo, is treated with the Mung bean nuclease. The fragment thus treated is then ligated to the vector pHREII giving rise to pHREIII.

3. Introduction of the Expression Cassette of a DNA Fragment of Interest into the Intron 3.

The first expression cassette of the fragment of DNA of interest comprises in sequence from 5' to 3' respectively:
(1) the TK promoter of the HSV virus,
(2) the neomycin gene, and
(3) the poly A region of the SV40 virus.

The XhoI-SalI fragment of 1.1 kb comprising the said expression cassette is isolated from the plasmid pMC1 neo (stratagene) is cloned in the vector pHREIII linearized by XhoI. The vector resulting from this is designated pHRE IV.

4. Cloning in an Adenoviral Vector and Infection of Host Cells

The NheI fragment comprising the transposition assembly (intron 3 into which is introduced the first neo expression cassette, flanked by adjacent 5' and 3' sequences of the human 28S RNA gene) and the second expression cassette of IPpo are isolated from the pHREIV vector. The purified fragment is treated with T4 polymerase before being inserted into the vector pXCX2 (Spessot et al., 1989, Virology, 168, 378–387).

The vector resulting from this is used to generate a recombinant adenovirus by the conventional methods, such as, for example, the method reported in Spessot et al. (1989, Virology, 168, 378–387). The recombinant adenoviral vector is constructed starting from a deletion mutant of the type 5 adenovirus (Thimmappaye et al. 1982, Cell, 31, 543–551). The recombinant adenoviral vector thus obtained is used to infect human cells in culture.

The cells are cultivated under the conventional conditions known to the person skilled in the art. 48 hours after infection, the cells are placed in a culture medium containing neomycin.

The presence of the neo gene in the cells can be checked by their resistance phenotype to neomycin and examined by Southern blot. The site-specific insertion of the integration cassette into the cellular genome can be examined by PCR. A primer complementary to a sequence of the human 28S rRNA gene which is not present in the transposition assembly (at the 5' end of the position 2324 or at the 3' end of the position 4438) and a primer complementary to a sequence of the integration cassette normally not present in the cellular genome (for example of intron 3 or of the expression cassette of the neo gene) will preferably be used. A PCR fragment of a uniquely defined size will be obtained in the case of site-specific integration of the integration cassette into the human 28S rRNA gene.

Example 3

Construction of a Replicative (Episomal) Plasmid Vector for Integration of the Neomycin Gene into the Human Genome The NheI fragment of Example 2.4 is inserted into the pREP4 vector (Grager et al., 1989, Gene, 81, 385–294; Invitrogen Corporation, British Bio-Technology Products LTD, Oxon, UK; reference V 004–50) at the level of the unique NheI site.

The vector resulting from this is transfected into a line of human cells in culture as indicated in Yates et al. (1985, Nature, 313, 812–815). In an indicative capacity, the line 293 is mentioned, embryonic human kidney line, available from ATCC. 48 hours after transfection, the cells are placed in a selective culture medium. The presence of the neo gene integrated into the cellular genome is verified as described in Example 2.4.

What is claimed is:

1. A delivery vehicle including a transposition assembly for the site-specific transfer of a DNA fragment of interest into the genome of a mammalian host cell, said transposition assembly comprising an integration cassette which is essentially formed by a mobile genetic element in the midst of which is inserted said DNA fragment of interest; wherein (i) said mobile genetic element is devoid of a long terminal repeat and comprises an open reading frame coding for an integrase and (ii) said integration cassette is capable of being integrated to an insertion site specific to said genetic mobile element, said insertion site being a target sequence situated in the ribosomal nuclear DNA of said host cell, and wherein said transposition assembly is:

a) encapsulated into a liposome or synthetic lipid type vector, or b) cloned into an expression vector.

2. The delivery vehicle of claim 1, wherein the mobile genetic element is selected from the group consisting of the mobile introns of class I, the mobile introns of class II, the retroposons of class R1, the retroposons of class R2 and the retroposons of class R3.

3. The delivery vehicle of claim 2, wherein the mobile introns of class I are selected from the group consisting of:

the intron 3 of *Physarum polycephalum,* Carolina strain;

the mobile intron of class I of Tetrahymena; and the mobile intron of class I of *Pneumocystis carinii.*

4. The delivery vehicle of claim 2, wherein the retroposon of class R2 is the retroposon of R2Bm of *Bombyx mori.*

5. The delivery vehicle of claim 2, wherein the retroposon of class R3 is the retroposon R3 of *Scaria coprophila.*

6. The delivery vehicle of claim 1, wherein said integrase is an endonuclease.

7. The delivery vehicle of claim 6, wherein the DNA fragment of interest is inserted into said open reading frame.

8. The delivery vehicle of claim 1, wherein the DNA fragment of interest is transcribed to RNA to (i) produce an anti-sense RNA or (ii) produce a protein of interest after translation of said RNA.

9. The delivery vehicle of claim 8, wherein the DNA fragment of interest is under the control of transcription regulation elements allowing the expression of said DNA fragment in the host cell.

10. The delivery vehicle of claim 9, wherein the transcription regulation elements comprise a promoter selected from the group consisting of promoters recognized by RNA polymerase I and by RNA polymerase II.

11. The delivery vehicle of claim 1, wherein said transposition assembly comprises, at the 5' end of the integration cassette a region identical to the sequences positioned at the 5' end of the said insertion site of the ribosomal nuclear DNA of the host cell; and at the 3' end of the integration cassette a region identical to the sequences positioned at the 3' end of the said insertion site of the ribosomal nuclear DNA of the host cell.

12. The delivery vehicle of claim 1, wherein the vector contains an expression cassette allowing the expression of a selection marker.

* * * * *